United States Patent
Culross

[11] Patent Number: 5,928,983
[45] Date of Patent: Jul. 27, 1999

[54] PROCESS FOR THE PREPARATION OF HIGH ACTIVITY CARBON MONOXIDE HYDROGENATION CATALYSTS AND THE CATALYST COMPOSITIONS

[75] Inventor: Claude C. Culross, Baton Rouge, La.

[73] Assignee: Exxon Research and Engineering Co, Florham Park, N.J.

[21] Appl. No.: 08/891,388

[22] Filed: Jul. 11, 1997

[51] Int. Cl.$^6$ .............................. B01J 31/04; B01J 23/38
[52] U.S. Cl. ........................ 502/170; 502/150; 502/325; 502/326; 502/327
[58] Field of Search .................................... 502/325, 326, 502/327, 150, 170

[56] References Cited

U.S. PATENT DOCUMENTS

| | | | |
|---|---|---|---|
| 4,065,543 | 12/1977 | Sare et al. | 423/240 |
| 4,113,658 | 9/1978 | Geus | 252/524 |
| 4,199,479 | 4/1980 | Wilkes | 252/457 |
| 4,568,663 | 2/1986 | Mauldin | 502/325 |
| 5,070,064 | 12/1991 | Hsu et al. | 502/325 |
| 5,217,938 | 6/1993 | Reinalda et al. | 502/325 |
| 5,391,531 | 2/1995 | Ward | 502/208 |

Primary Examiner—Michael Lewis
Assistant Examiner—Alexander G. Ghyka

[57] ABSTRACT

A process for the preparation of a novel highly active, highly selective catalyst useful for conducting carbon monoxide hydrogenation reactions, particularly Fischer-Tropsch reactions, the catalyst per se, and process for use of such catalyst in conducting carbon monoxide hydrogenation reactions, particularly Fischer-Tropsch synthesis reactions. The catalyst is prepared by contacting together, preferably by dispersing in a liquid, a preformed, particulate refractory inorganic oxide support, preferably a fumed silica support, compound or salt of a catalytic metal, or metals, i.e., a metal selected from Groups IB, IIB, VIIB or VIII of the Periodic Table, preferably cobalt, an oxidizable alcohol, oxidizable aldehyde, or oxidizable ketone promoter, suitably glyoxal, and an oxidant sufficient to react with the promoter and convert the metal, or metals, to an insoluble highly dispersed metal carboxylate which is deposited and supported on the support. The solids are recovered, and heated at an elevated temperature to reduce the catalytic metal, or metals, to the zero-valent state and form the catalyst composite. This catalyst in its reduced form is very active, and selective, in conducting carbon monoxide hydrogenation reactions, particularly in converting a mixture of hydrogen and carbon monoxide to $C_5+$ hydrocarbons, on contact of the gaseous mixture with the catalyst at reaction conditions.

15 Claims, No Drawings

PROCESS FOR THE PREPARATION OF HIGH ACTIVITY CARBON MONOXIDE HYDROGENATION CATALYSTS AND THE CATALYST COMPOSITIONS

FIELD OF THE INVENTION

This invention relates to a process for the preparation of novel, highly active, highly selective catalysts useful for conducting carbon monoxide hydrogenation reactions, particularly Fischer-Tropsch reactions. It also relates to the catalyst, and to a process utilizing the catalyst for conducting such reactions; especially catalysts useful for the production of transportation fuels from synthesis gas.

BACKGROUND

There exists a continuing interest in developing processes for conducting carbon monoxide hydrogenation reactions, especially in a more efficient Fischer-Tropsch process, or process for the catalyzed production of $C_5+$ liquid hydrocarbons from synthesis gas, or mixtures of hydrogen and carbon monoxide. This interest is driven primarily by the need to utilize alternative fuel sources such as coal and natural gas as raw materials.

SUMMARY OF THE INVENTION

The present invention, which satisfies this need and others, relates to a process for the preparation of a novel carbon monoxide hydrogenation catalyst, especially a novel Fischer-Tropsch catalyst, to said novel catalyst, and to a process for use of such catalyst for conducting carbon monoxide hydrogenation reactions; particularly Fischer-Tropsch synthesis reactions, or reactions for the production of $C_5+$ liquid hydrocarbons from hydrogen and carbon monoxide. The catalyst is a composite of a catalytic metal, or metals, particularly a metal, or metals, selected from Groups IB, IIB, VIIB and VIII of the Periodic Table Of The Elements (Sargent-Welch Scientific Company; Copyright 1968), preferably cobalt, or cobalt and another metal, or metals, and a preformed, particulate refractory inorganic oxide support, preferably a silica support, and more preferably a fused, flame synthesized, or fumed silica support on which the catalytic metal, or metals, has been highly dispersed as an insoluble carboxylate salt of said catalytic metal, or metals, prior to reduction to the zero-valent state. The catalyst is formed by contacting together, preferably dispersing in a liquid, suitably water or other solvent, the preformed support, a compound or salt of the catalytic metal, or metals, an oxidizable alcohol, oxidizable aldehyde, or oxidizable ketone promoter, and an oxidant sufficient to oxidize said promoter and convert the catalytic metal, or metals, to an insoluble highly dispersed carboxylate salt of said catalytic metal, or metals, which is deposited and supported on said support to form the catalyst composite. The solids are dried by heating, either by heating in a vacuum or at atmospheric pressure, and then subsequently treated by heating at more elevated temperatures adequate to reduce the catalytic metal, or metals, to the zero-valent state; generally by heating in a vacuum or an inert atmosphere. Alternatively, a zero-valent metal, or metals, can be formed by calcining and then reducing in hydrogen, or only by reducing in hydrogen, without prior calcination. The catalyst in its reduced form, is more active, and more selective, in conducting carbon monoxide hydrogenation, or Fischer-Tropsch reactions, at the same reaction conditions than catalysts of similar composition, similarly prepared except that the catalyst has not been contacted and treated with said oxidizable alcohol, oxidizable aldehyde, or oxidizable ketone promoter.

The reaction wherein the insoluble metal carboxylate is formed, e.g., as per the equation

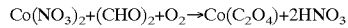

$$Co(NO_3)_2 + (CHO)_2 + O_2 \rightarrow Co(C_2O_4) + 2HNO_3$$

and the formation of the zero-valent metal, or metals, may involve separate heating steps. Heating the solids at low temperature, i.e., from about ambient to about 120° C., sufficient to remove the liquid component and dry the solids defines the drying step (Excessive temperature is to be avoided because metals dispersion can be adversely affected.). The reaction step, generally conducted at temperatures ranging from about ambient to about 200° C., preferably from about 100° C. to about 160° C., can optionally precede the drying step, follow the drying step, or conducted simultaneously with the drying step. Drying, or at least partial drying, generally precedes the reaction where ambient, or near ambient heating is employed. Reaction is simultaneous with drying at temperatures above ambient; and preferably the drying and reaction steps are conducted simultaneously. A heating of the solids at more elevated temperature (whether in an inert atmosphere, under vacuum, under a reducing atmosphere or calcination in air), separate and apart from those which effect the reaction and drying steps, is required to reduce the catalytic metal, or metals, to the zero-valent state and form the catalyst composite; with treatment under a reducing atmosphere at elevated temperature being required after calcination. Thus, after the reaction and drying steps, the solids are heated, preferably to an initial temperature of about 330° C. to about 350° C., and then preferably to a final temperature of about 375° C. to about 400° C. to transform most of the metal, or metals, carboxylate to metallic metal, to form the zero-valent metal, or metals. Where adequate reduction of the catalytic metal, or metals, does not occur however, a catalyst can be heated in a reducing atmosphere, such as hydrogen, without prior calcination, or heated in an oxidizing atmosphere in a first step to form an oxide of the catalytic metal, or metals, and the catalyst then heated in a reducing atmosphere in a second step to bring the catalytic metal, or metals, to the zero-valent state. Preferably, in the practice of this invention, it is sufficient to heat the paste or slurry to simultaneously conduct the drying and heating reactions, and then further elevate the temperature to complete formation of the catalyst composite.

Catalytic metals useful for the formation of catalysts pursuant to the practice of this invention include, e.g., metals from Group IB, exemplary of which is copper; metals from Group IIB, exemplary of which are zinc and cadmium; metals from Group VIIB, exemplary of which is rhenium; and metals from Group VIII, inclusive of both the noble metals, exemplary of which is ruthenium, and Iron Group metals, exemplary of which are iron, cobalt and nickel. The Iron Group metals, preferably cobalt, are particularly useful in the formation of Fischer-Tropsch catalysts.

A catalyst found particularly active in conducting Fischer-Tropsch reactions is formed by dispersing in a liquid, or solvent, suitably water, a preformed particulate silica support, preferably a fumed silica support, a compound, or salt of a catalytic metal, or metals, preferably an Iron Group metal, notably cobalt, or compounds or salts of one or more of an Iron Group metal and another metal, or metals, an oxidizable alcohol, oxidizable aldehyde, or oxidizable ketone promoter, and oxidant in molar amount sufficient to react with said promoter to convert the metal, or metals, to an insoluble highly dispersed carboxylate of the metal, or metals, which is deposited upon the support. The catalyst is then dried, and reduced. For example, in preparing a cobalt-silica catalyst, an aqueous solution of cobalt nitrate and glyoxal can be mixed with, and impregnated into a preformed particulate silica solids support e.g., fumed silica support solids, up to or beyond the point of incipient wetness of the solids with the solution to produce a slurry or paste; in a single step, or in a sequence of steps. The cobalt nitrate in this instance supplies both the catalytic metal, i.e., the cobalt, and the oxidant, i.e., the nitrate anion. Typically, in the preparation, e.g., where the cobalt is a cobalt nitrate in aqueous solution, the cobalt solution is of a purple coloration, gradually lightening to a pink coloration as gaseous oxides of nitrogen are evolved. As reaction proceeds, dark purple cobalt nitrate is replaced by pink cobalt oxalate. The gas phase above the reaction medium changes from clear and colorless to dark reddish-brown. Evolution of the gases from the slurry or paste ceases on completion of the reaction which converts the cobalt to a highly dispersed, and insoluble form of cobalt carboxylate. The catalyst is preferably subjected to a simultaneous drying-reaction step, e.g., by heating the solids to a temperature of 100° C. for a period of 4–8 hours. Thereafter, the solids are heated to a higher temperature, e.g., to about 350° C., and then to 400° C. for a period adequate to bring the cobalt to its zero-valent state. Generally the catalyst is heated in a vacuum or an inert atmosphere. Optionally, the metal carboxylate-containing solids can be treated in a reducing atmosphere, suitably hydrogen, without prior calcination to bring the metal component of the catalyst to its zero-valent state. If necessary however, the metal, or metals component of the catalyst can be first oxidized, and then reduced in a subsequent step as by contact with hydrogen. A cobalt catalyst produced in this manner, dried, and reduced, has been found to be at least about 1.5 times more active, and generally more selective, in converting a mixture of hydrogen and carbon monoxide to $C_5+$ hydrocarbons than a cobalt catalyst of similar composition, similarly prepared except that the silica support component of the catalyst is not a fumed silica, or is in fact a cobalt catalyst constituted of a fumed silica component which had not been contacted, and treated with the glyoxal.

DETAILED DESCRIPTION

The catalyst composite is prepared by contacting a preformed particulate refractory inorganic oxide support, preferably silica, and more preferably fumed silica solids, with a liquid, or solution, containing a compound, or salt of an Iron Group metal, i.e., a compound, or salt of iron, cobalt, nickel, or mixture thereof, an oxidizable alcohol, oxidizable aldehyde, or oxidizable ketone promoter, and an oxidant. This contacting procedure can be carried out in one, or in a series of steps. Compounds suitable as sources of the Iron Group metal are, e.g., cobaltous hydroxyquinone, cobalt acetate, iron acetate, nickel acetate, nickel acetylacetonate, nickel naphthenate, and the like; and hydrogen peroxide, $H_2O_2$, and nitric acid, $HNO_3$, are exemplary of oxidants. Some compounds, e.g., cobalt nitrate, can provide both the required catalytic metal, and the oxidant. In preparation of the catalyst, the molar amount of promoter is sufficient to react with the metal, or metals, compound or compounds to form an insoluble highly dispersed carboxylate salt of the metal, or metals, which is deposited on the solids support component. The initial consistency of the mixture ranges from a slurry to a paste, depending upon the nature of the solids, and the ratio of solution to solids which is adjusted according to the desired final metal content. In the reaction, the molar amount of promoter:metal ranges generally from about 0.01:1 to about 5:1, preferably from about 0.5:1 to about 2:1, based on the stoichiometric amount of the promoter required for complete reaction with the metal compound, or compounds. The drying step is conducted at temperature ranging from about ambient to about 120° C. The reaction required to form the insoluble metal carboxylate can be done after drying at ambient temperature, or simultaneously with drying at temperatures above ambient; preferably the latter. The reaction can take place at pressures below atmospheric, above atmospheric, or at atmospheric or ambient pressure. In the reaction, gaseous oxides and acids are evolved, with the pH of the slurry being very highly acidic. The gaseous oxides and acids are nitrogen compounds where the oxidant is a nitrogen compound, or nitrogen moiety. Thus, in such reaction $HNO_3$ is believed to be a by-product, the NO by-product reacting instantly with $O_2$ under air to produce $NO_2$ with the $NO_2$ reacting with water to produce additional $HNO_3$ over and above that which is a direct by-product. Accordingly, as will be appreciated it is not feasible to precisely define a constant slurry pH where $HNO_3$ is constantly being generated during reaction, but with complete reaction of the nitrate salt, the amount of $HNO_3$ generated is generally sufficient to lower pH to about 1.0 or below 0.0. However, the extent of evolution of nitrogen oxides and acids, that is, the extent of reaction, may range as low as 5% of full reaction, and still produce the benefit of higher activity; but, more preferably the extent of the reaction ranges from 70% of full reaction to full reaction. In the case where there is sufficient promoter for reaction with all metal, or metals, compound or compounds wherein the amount of cobalt nitrate is sufficient to reach a loading of 40 wt % (wt. %, dry basis; Co assumed to be in the form of $Co_3O_4$), and reaction proceeds to 5% completion, the amount of $HNO_3$ generated is sufficient to lower pH to about 1.0. The catalyst prior to use is dried; warming, suitably by boiling off the liquid, continuing the warming and recovering the dry particulate catalytic solids. The metal, or metals, component of the catalyst can be reduced and activated for use in conducting the Fischer-Tropsch reaction, as by oxidation of the catalyst with subsequent contact with a reducing agent; suitably hydrogen. Or, the catalyst can be contacted with hydrogen (without prior oxidation), or heated to zero-valent metal under vacuum or inert atmosphere. For example, where the metal is cobalt, heating at about 330° C. is needed to form zero-valent metal under vacuum or inert, and heating to 400° C. is generally adequate to complete the formation.

A wide number of refractory inorganic oxide supports can be employed in the practice of this invention, these including, e.g., alumina, silica, silica-alumina, titania, and zirconia, and their mixed oxides; with silica being preferred, especially a fumed silica. The more preferred support component of the catalyst is constituted of a fused, flame synthesized, or fumed silica; a silica formed by hydrolysis of silicon tetrachloride vapor in a flame of hydrogen and oxygen at about 1800° C. In making silica of this type, molten spheres of silica are formed in the combustion process, the diameters of the spheres being varied but averaging about 7 to 40 millimicrons. The molten spheres of fumed silica, during their manufacture, fuse with one another to form three dimensional branched, chain-like aggregates of approximately 0.1 to 0.5 micron in length. Cooling takes place very quickly, limiting the growth and ensuring that the fumed silica is amorphous. These aggregates in turn form agglomerates ranging in size from about 0.5 to about 44 microns.

The fumed silica is low in bulk density ranging generally from about 0.04 g/cc to about 0.08 g/cc, and of open structure with very high external surface area. Unlike the more common precipitated silicas the surface area of the fumed silica is almost exclusively external; surface areas ranging between about 50 $m^2/g$ and about 400 $m^2/g$ [as measured by the nitrogen adsorption method of S. Brunauer, P. H. Emmet and I. Teller, *J. Am Chemical Society*, vol. 60, page 309 (1938)]. Although many commercially available fumed silicas are suitable, preferred fumed silicas are those available under the name of CAB-O-SIL® and AEROSIL®. (CAB-O-SIL® is a registered trademark of Cabot Corporation, and AEROSIL® is a registered trademark of Degussa). Such silicas have been found of high quality and are readily dispersable. The large external surface areas and pore volumes of these silicas permit high metals loadings, while retaining high pore volumes, this permitting high productivity with low pore diffusion limitations. The bulk density which, relatively speaking, remains low after metals impregnation in comparison to catalysts formed from precipitated or spray dried supports, permits passive fluidization in a gas-ebullated slurry reactor with either no or at least minimal use of added reactor internals to assist fluidization (downcomers, lift tubes, and so forth). The supports can be used in the form of pills, pellets, extrudates, powders, and the like to form catalysts.

The promoter is characterized as an oxidizable alcohol, oxidizable aldehyde, or oxidizable ketone. The promoter is commonly supplied in solution, a source which supplies the required promoter, and all or some part of the dispersing medium. Glyoxal, or dialdehyde, is a preferred promoter. Alcohols, aldehydes and ketones suitable as promoters for the practice of this invention are those which contain generally from about 1 to about 18 carbon atoms, preferably from 1 to about 6 carbon atoms, per molecule, these including both acyclic and cyclic mono- and polyhydroxy alcohols, aldehydes and ketones, exemplary of which are such vicinal diols as 1,2-dihydroxycyclohexane and the like; cyclic 1,2-diones such as cyclohexane-1,2-dione and the like; ∂-hydroxyaldehydes such as hydroxyacetaldehyde; glyoxylic acid; ∂-hydroxycarboxylic acids, such as glycolic acid and the like; dialdehydes such as propanolonal and the like; and polyaldehydes such as triformylmethane and the like. These compounds are oxidized to form an insoluble highly dispersed carboxylate form of the metal, or metals, on the solids support surface; gaseous oxides and acids generally being evolved during the reaction to form polyfunctional carboxylic acids which react in situ with the metal, or metals, compound or compounds of the catalyst to precipitate on the surface of the support a highly dispersed carboxylic acid salt, or salts, of the metal, or metals. Even where a nitrate, or nitric acid is used as an oxidant the carboxylic acid salt, or salts of the metal, or metals, deposited on the support is essentially nitrogen free.

The metal, or metals, e.g., iron, cobalt or nickel, can be loaded upon a support component, especially a catalyst formed from a fused silica component, in concentrations ranging from about 10 percent to about 80 percent, and greater, preferably from about 30 percent to about 60 percent, measured as elemental metal, based on the total weight of the catalyst [wt. %; dry basis]. Typically, the metal, or metals, is composited with the support by impregnation of the support up to or beyond the point of incipient wetness with a solution of a compound, or salt, of the catalytic metal, or metals, while retaining relatively high pore volumes as related to the total amount of the metal, or metals, loaded onto or present on the catalyst. Metals loadings upon a fused silica support component range generally from about 0.000222 to about 0.0105 g metal/$m^2$ support surface area, preferably from about 0.000857 to about 0.00395 g metal/$m^2$ support surface area; loadings which are typically 1 percent to about 20 percent higher than achieved by treatment at similar conditions, with a similar solution of a compound, or salt of a similar metal, or metals, of a silica support of similar composition except that the silica is not fumed silica. The dried solids, with the highly dispersed, high loadings of insoluble metal carboxylate, are readily oxidizable on contact with an oxygen-containing gas, and reducible on contact with hydrogen; or reducible by heating under vacuum or inert, without previous oxidation of the catalyst. Calcination of the catalyst is unnecessary, since both the carboxylate and nitrate salts readily reduce to zero-valent metal.

Various oxidants are suitable for initiating oxidation of the oxidizable alcohol, oxidizable aldehyde, and oxidizable ketone promoters, exemplary of which are hydrogen peroxide, $H_2O_2$, and nitric acid, $HNO_3$. The nitrate anion itself is a suitable oxidant, as where the compound or salt of the catalytic metal itself provides a nitrate anion, e.g., $Co(NO_3)_2$. Where however, the catalytic metal is supplied by a compound or salt which does not provide an anion oxidant, the oxidant must be added with the compound or salt of the catalytic metal. For example, where cobalt acetate is used as the source of the catalytic metal, an oxidant, e.g., $H_2O_2$ or $HNO_3$, must be supplied with the cobalt acetate. Quite commonly, oxidants are supplied in liquid solutions, e.g., $H_2O_2$ or $HNO_3$ in water. An oxidant in this form can supply both the required oxidant, and liquid within which the oxidant, compound or salt of the catalytic metal, or metals, support, and promoter are dispersed, or dissolved.

Various metals can be composited with the catalytic metal, or metals, to promote, or modify the activity, or selectivity, of a given catalyst for conducting a carbon monoxide hydrogenation, or Fischer-Tropsch reaction. For example, although an Iron Group metal/silica catalyst is highly active for the conversion of synthesis gas, and highly selective for the production of $C_5+$ hydrocarbons, an additional metal, or metals, can be included as a promoter, or modifier if desired. Ruthenium or other Group VIII noble metal, rhenium or the like may thus be included, the amount thereof ranging up to a 1:12 ratio of promoter metal to Iron Group metal (wt. basis), preferably up to a 1:80 ratio of promoter metal to Iron Group metal (wt. basis). Thus, a Ru:Co ratio of about 1:80 and a Re:Co ratio of about 1:12 provides highly active catalysts. In general, it is preferred to codeposit the promoter metal, or metals, onto the silica support simultaneously with the catalytic metal, or metals, e.g., rhenium and an Iron Group metal, or metals. This can be done, e.g., by using a compound, or salt of the promoter metal, or metals, added with a compound, or salt of the catalytic metal, or metals, dissolved in the same solvent; or the promoter metal, or metals, may be deposited after deposition of the Iron Group metal, or metals, by dissolving a compound, or salt of the promoter metal, or metals, in a different solution and impregnating the preformed Iron Group metal/silica catalyst composite. Water is the preferred dispersing agent, or solvent, but a wide variety of organic, or hydrocarbons, may also be suitable as dispersing agents, or solvents; i.e., for dispersing the particulate support, e.g., fumed silica, compound, or for dissolving the salt of the Iron Group metal, or metals, added promoter metal, or metals, and oxidant. Exemplary of selectively useful solvents are straight chain, branched chain or cyclic aliphatic hydrocarbons, saturated or unsaturated, substituted or unsubstituted, such as hexane, cyclohexane, methyl cyclohexane, and the like; aromatic hydrocarbons substituted or unsubstituted, such as benzene, toluene, xylenes, ethylbenzene, cumene, and the like.

In conducting a carbon monoxide hydrogenation, or Fischer-Tropsch reaction, the dry catalyst is charged into a reaction zone, and the catalyst activated in situ by heating, or if required by oxidation and subsequent reduction with hydrogen; or the dry catalyst is activated ex situ by heating, or if required by oxidation and subsequent reduction with hydrogen, and then charged into the reaction zone. The activated catalyst may be employed as a fixed bed, a moving bed, ebulating bed, fluidized bed, or slurry bed. In a Fischer-Tropsch reaction, synthesis gas, or mixture of hydrogen and carbon monoxide, at suitable $H_2:CO$ molar ratio, is contacted with the bed of reduced catalyst, and reacted at reaction conditions. Generally, the molar ratio of $H_2:CO$ ranges from about 0.5:1 to about 3.0:1, preferably from about 1.6:1 to about 2.5:1, reaction temperatures are elevated, ranging from about 180° C. to about 300° C., preferably from about 190° C. to about 260° C., and pressures range from about 100 psig to about 1000 psig, preferably from about 180 psig to about 600 psig.

The invention, and its principle of operation, will be better understood by reference to the following examples which illustrate specific and preferred embodiments, and present comparative data. All parts are in terms of weight except as otherwise specified.

EXAMPLES

The example immediately following describes three catalyst preparations, 1(a), 1(b) and 1(c), the recovery from solution of the treated solids, and the drying and reaction of the solids by heating the recovered solids at different temperatures. The activity of the prepared catalysts was measured by $O_2$ chemisorption. These data demonstrate that a one-step, or single stage drying-reaction at moderately low temperature is adequate and after reduction to the zerovalent state, produces the more active catalysts. In the description the designation in the subtitle "1(a) 100° C." refers to a drying-reaction preparation made at 100° C.; "1(b) 50+100° C." refers to a two-step drying-reaction preparation made by heating the solids overnight at 50° C., and again at 100° C. overnight; and "1(c) 200° C." refers to a drying-reaction preparation made in a single step at 200° C.

EXAMPLE 1

1(a) 100° C.:

A solution was made from 50.59 g $Co(NO_3)_2 \cdot 6H_2O$ (Aldrich, 99%), 1.80 g aqueous $HReO_4$ (Aldrich; 65–70 wt %), and 26.48 g aqueous glyoxal (Aldrich; 40 wt %; 1.05:1 mol:mol ratio to $Co(NO_3)_2 \cdot 6H_2O$).

75.05 g of the solution was mixed with 10.00 g fumed $SiO_2$ (EH-5 grade; Cabot Corporation), and the resulting mixture was placed into a vacuum oven set at 100° C. for 4 hr. The friable solid was reduced to a powder by milling one minute in a small laboratory analytical mill (Janke & Kunkel).

The milled solid had a loose bulk density of 1.201 g/cc, surface area of 127 $m^2$/g, pore volume of 0.2238 ml/g, and analyzed for 9.15 wt % C, 23.87 wt % Co and 1.04 wt % N (90.8% reaction). Temperature quenched $O_2$ chemisorption after standard 450° C. reduction was 1492 $\mu$mol $O_2$/g catalyst; O/Co=0.737, mol/mol.

1(b) 50+100° C.:

A solution was made from 50.56 g $Co(NO_3)_2 \cdot 6H_2O$ (Aldrich, 99%), 1.78 g aqueous $HReO_4$ (Aldrich; 65–70 wt %), and 26.48 g aqueous glyoxal (Aldrich; 40 wt %; 1.05:1 mol:mol ratio to $Co(NO_3)_2 \cdot 6H_2O$). 75.04 g of the solution was mixed with 10.00 g fumed $SiO_2$ (EH-5 grade; Cabot Corporation). The mixture was placed into a vacuum oven set at 50° C. overnight, then the resulting dark pink (indicating extensive reaction) damp cake was placed into a vacuum oven set at 100° C. until the next morning. The friable solid was reduced to a powder by milling one minute in a small laboratory analytical mill (Janke & Kunkel).

The milled solid had a loose bulk density of 1.0567 g/cc, surface area of 106 $m^2$/g, pore volume of 0.1957 ml/g, and analyzed for 8.92 wt % C, 23.40 wt % Co and 1.08 wt % N (90.3% reaction). Temperature quenched $O_2$ chemisorption after standard 450° C. reduction was 1531 $\mu$mol $O_2$/g catalyst; O/Co=0.716, mol/mol.

1(c) 200° C.:

A solution was made from 50.56 g $Co(NO_3)_2 \cdot 6H_2O$ (Aldrich, 99%), 1.79 g aqueous $HReO_4$ (Aldrich; 65–70 wt %), and 26.47 g aqueous glyoxal (Aldrich; 40 wt %; 1.05:1 mol:mol ratio to $Co(NO_3)_2 \cdot 6H_2O$).

75.04 g of the solution was mixed with 10.00 g fumed $SiO_2$ (EH-5 grade; Cabot Corporation), and the resulting mixture was placed into a vacuum oven set at 200° C. for 4 hr. The friable solid was reduced to a powder by milling one minute in a small laboratory analytical mill (Janke & Kunkel).

The milled solid had a loose bulk density of 0.945 g/cc, surface area of 144 $m^2$/g, pore volume of 0.2944 ml/g, and analyzed for 9.55 wt % C, 27.27 wt % Co and <0.5 wt % N (>96.1% reaction). Temperature quenched $O_2$ chemisorption after standard 450° C. reduction was 610 $\mu$mol $O_2$/g catalyst; O/Co=0.264, mol/mol.

It is evident from these data (summarized in Tables 1 and 2) that the catalyst made by the single stage drying-reaction at 100° C. is superior to that made by a single stage drying-reaction at 200° C. On the other hand, the catalyst made by conducting the drying-reduction in two stages quite obviously offers no advantage over the single step preparation of 1(a). The time required for the preparation is longer. The one step drying-reaction procedure at relatively low temperature is preferred.

The following Example 2 presents several additional catalyst preps as in 1(a), supra, using different, both shorter and longer, time periods for the drying-reaction procedure. These preps describe catalysts made by carrying out the drying-heating step at heating time of 1 hour and 8 hours, and overnight in a vacuum followed by 100° C. for 8 hours. The catalysts made in these runs are contrasted with those of Example 1; noting particularly Example 1(a) which differs from the Example 2 preps only in the time period of the drying-reduction step.

EXAMPLE 2

2(a) 100° C./1hr:

A solution was made from 50.57 g $Co(NO_3)_2 \cdot 6H_2O$ (Aldrich, 99%), 1.80 g aqueous $HReO_4$ (Aldrich; 65–70 wt %), and 26.49 g aqueous glyoxal (Aldrich; 40 wt %; 1.05:1 mol:mol ratio to $Co(NO_3)_2 \cdot 6H_2O$).

75.08 g of the solution was mixed with 10.00 g fumed $SiO_2$ (EH-5 grade; Cabot Corporation), and the resulting mixture was placed into a vacuum oven set at 100° C. for 1 hr. The friable solid—which was a rose-pink indicative of reaction—was reduced to a powder by milling one minute in a small laboratory analytical mill (Janke & Kunkel).

The milled solid had a loose bulk density of 1.1826 g/cc, surface area of 111 m$^2$/g, pore volume of 0.1666 ml/g, and analyzed for 8.94 wt % C, 23.06 wt % Co and 1.57 wt % N (85.7% reation). Temperature quenched $O_2$ chemisorption after standard 450° C. reduction was 1361 $\mu$mol $O_2$/g catalyst; O/Co=0.696 mol/mol.

2(b) 100° C./8 hr:

A solution was made from 50.57 g $Co(NO_3)_2 \cdot 6H_2O$ (Aldrich, 99%), 1.79 g aqueous $HReO_4$ (Aldrich; 65–70 wt %), and 26.46 g aqueous glyoxal (Aldrich; 40 wt %; 1.05:1 mol:mol ratio to $Co(NO_3)_2 \cdot 6H_2O$).

75.06 g of the solution was mixed with 10.00 g fumed $SiO_2$ (EH-5 grade; Cabot Corporation) and the resulting mixture was placed into a vacuum oven set at 100° C. for 8 hr. The friable solid was reduced to a powder by milling one minute in a small laboratory analytical mill (Janke & Kunkel).

The milled solid had a loose bulk density of 1.0591 g/cc, surface area of 166 m$^2$/g, pore volume of 0.1953 ml/g, and analyzed for 9.81 wt % C, 24.98 wt % Co and 0.81 wt % N (93.2% reaction). Temperature quenched $O_2$ chemisorption after standard 450° C. reduction was 1676 $\mu$mol $O_2$/g catalyst; O/Co=0.791, mol/mol.

2(c) Vacuum drying overnight +100° C./8 hr:

A solution was made from 50.57 g $Co(NO_3)_2 \cdot 6H_2O$ (Aldrich, 99%), 1.80 g aqueous $HReO_4$ (Aldrich; 65–70 wt %), and 26.48 g aqueous glyoxal (Aldrich; 40 wt %; 1.05:1 mol:mol ratio to $Co(NO_3)_2 \cdot 6H_2O$).

75.06 g of the solution was mixed with 10.00 g fumed $SiO_2$ (EH-5 grade; Cabot Corporation), and the resulting mixture was placed into a vacuum oven set at room temperature overnight, then at 100° C. for 8 hr. The friable solid was reduced to a powder by milling one minute in a small laboratory analytical mill (Janke & Kunkel).

The milled solid had a loose bulk density of 0.969 g/cc, surface area of 133 m$^2$/g, pore volume of 0.2172 ml/g, and analyzed for 9.16 wt % C, 23.26 wt % Co and 0.84 wt % N (92.4% reaction). Temperature quenched $O_2$ chemisorption after standard 450° C. reduction was 1361 $\mu$mol $O_2$/g catalyst; O/Co=0.690, mol/mol.

The results of runs made with the catalyst prepared in both Examples 1 and 2 are summarized in Tables 1 and 2.

TABLES 1 AND 2

| EXAMPLES | DRYING TEMPS, ° C. | DRYING TIMES, hr | % REACTION[1] | O/Co, mol/mol[2] |
|---|---|---|---|---|
| 1(a)[4] | 100 | 4 | 90.8 | 0.737 |
| 1(b) | 50 + 100 | O/N + O/N[3] | 90.3 | 0.716 |
| 1(c) | 200 | 4 | >96.1 | 0.264 |
| 2(a) | 100 | 1 | 85.7 | 0.696 |
| 1(a)[4] | 100 | 4 | 90.8 | 0.737 |
| 2(b) | 100 | 8 | 93.2 | 0.791 |
| 2(c) | R.T[5] + 100 | O/N + 8 | 92.4 | 0.690 |

Notes (Tables 1 and 2):
[1]Calculated from elemental analyses for Co and N, assuming that N is present as the cobalt precursor, $Co(NO_3)_2$.
[2]A standard test of $O_2$ chemisorption (with temperature quenching at −77° C. to minimize oxidation) preceded by a standard 450° C. reduction routine.
[3]O/N = overnight, generally about 17–18 hr.
[4]Note that 1(a) appears twice in this table.
[5]R.T. = room temperature Several conclusions can be made from these data, as evidenced particularly by the mol/mol ratio of O/Co. It is clear that high dispersion is obtained at drying-reaction times as short as an hour; that dispersion improves up to 8 hr, that the optimum time could be somewhere around 8 hr. and may be between 8 hr and ~17 hr. (overnight), or even beyond 17 hr; that immediate drying-reaction at 100° C. is equal to or better than 100° C. drying-reaction which has been preceded by an overnight period at room temperature; that % reaction tracks with time in the 1-4-8 hr series.

The following describe additional catalyst preparations, i.e., 3(a)/3(b) and 3(c)/3(d), respectively, wherein in all cases oxidant is the nitrate anion, though in some cases nitric acid is additionally added. The added nitric acid is shown to increase the rate of reaction, but diminish O/Co.

EXAMPLE 3

3(a) 6 hr at R.T +100° C./Overnight (atmospheric pressure) with no added $HNO_3$:

A solution was made from 101.12 g $Co(NO_3)_2 \cdot 6H_2O$ (Aldrich, 99%), 3.55 g aqueous $HReO_4$ (Aldrich; 65–70 wt %), and 52.96 g aqueous glyoxal (Aldrich; 40 wt %; 1.05:1 mol:mol ratio to $Co(NO_3)_2 \cdot 6H_2O$).

150.10 g of the solution was mixed with 20.00 g fumed $SiO_2$ (EH-5 grade; Cabot Corporation), and the resulting mixture was allowed to stand at room temperature for 6 hr then placed into a muffle furnace set at 100° C. overnight. The friable solid was reduced to a powder by milling one minute in a small laboratory analytical mill (Janke & Kunkel).

The milled solid had a loose bulk density of 1.172 g/cc, surface area of 236 m$^2$/g, pore volume of 0.4915 ml/g, and analyzed for 9.02 wt % C, 21.47 wt % Co and 1.33 wt % N (87.0% reaction). Temperature quenched $O_2$ chemisorption after standard 450° C. reduction was 1327 $\mu$mol $O_2$/g catalyst; O/Co=0.728, mol/mol.

3(b) 6 hr at R.T +100° C./Overnight (atmospheric pressure) with 0.2:1 $HNO_3$:Glyoxal (mol/mol):

A solution was made from 101.12 g $Co(NO_3)_2 \cdot 6H_2O$ (Aldrich, 99%), 3.55 g aqueous $HReO_4$ (Aldrich; 65–70 wt %), and 52.96 g aqueous glyoxal (Aldrich; 40 wt %; 1.05:1 mol:mol ratio to $Co(NO_3)_2 \cdot 6H_2O$), and 6.58 g concentrated $HNO_3$ (Mallinckrodt, 70.2 wt %).

150.15 g of the solution was mixed with 20.00 g fumed $SiO_2$ (EH-5 grade; Cabot Corporation), and the resulting mixture was allowed to stand at room temperature for 6 hr, then placed into a muffle furnace at 100° C. overnight. The friable solid was reduced to a powder by milling one minute in a small laboratory analytical mill (Janke & Kunkel).

The milled solid had a loose bulk density of 0.901 g/cc, surface area of 115 m$^2$/g, pore volume of 0.2380 ml/g, and analyzed for 8.82 wt % C, 21.10 wt % Co and 0.68 wt % N (93.2% reaction). Temperature quenched $O_2$ chemisorption after standard 450° C. reduction was 1036 $\mu$mol $O_2$/g catalyst; O/Co=0.579, mol/mol.

3(c) Overnight at R.T. +100° C./7 hr (atmospheric pressure) with no added $HNO_3$:

A solution was made from 101.14 g $Co(NO_3)_2 \cdot 6H_2O$ (Aldrich, 99%), 3.60 g aqueous $HReO_4$ (Aldrich; 65–70 wt %), and 52.98 g aqueous glyoxal (Aldrich; 40 wt %; 1.05:1 mol:mol ratio to $Co(NO_3)_2 \cdot 6H_2O$).

150.11 g of the solution was mixed with 20.00 g fumed $SiO_2$ (EH-5 grade; Cabot Corporation), and the resulting mixture was allowed to stand at room temperature overnight, then placed into a muffle furnace set at 100° C. for 7 hr. The friable solid was reduced to a powder by milling one minute in a small laboratory analytical mill (Janke & Kunkel).

The milled solid had a loose bulk density of 1.0192 g/cc, surface area of 167 m²/g, pore volume of 0.4676 ml/g, and analyzed for 8.88 wt % C, 22.15 wt % Co and 1.38 wt % N (86.9% reaction). Temperature quenched $O_2$ chemisorption after standard 450° C. reduction was 1367 μmol $O_2$/g catalyst; O/Co=0.727, mol/mol.

3(d) Overnight at R.T. +100° C./7 hr (atmospheric pressure) with 0.2:1 $HNO_3$:Glyoxal (mol/mol):

A solution was made from 101.14 g $Co(NO_3)_2 \cdot 6H_2O$ (Aldrich, 99%), 3.56 g aqueous $HReO_4$ (Aldrich; 65–70 wt %), and 52.96 g aqueous glyoxal (Aldrich; 40 wt %; 1.05:1 mol:mol ratio to $Co(NO_3)_2 \cdot 6H_2O$), and 6.56 g concentrated $HNO_3$ (Mallinckrodt, 70.2 wt %).

150.15 g of the solution was mixed with 20.00 g fumed $SiO_2$ (EH-5 grade; Cabot Corporation), and the resulting mixture was allowed to stand at room temperature overnight, then placed into a muffle furnace set at 100° C. for 7 hr. The friable solid was reduced to a powder by milling one minute in a small laboratory analytical mill (Janke & Kunkel).

The milled solid had a loose bulk density of 0.931 g/cc, surface area of 123 m²g, pore volume of 0.5736 ml/g, and analyzed for 9.16 wt % C, 22.78 wt % Co and 0.80 wt % N (92.6% reaction). Temperature quenched $O_2$ chemisorption after standard 450° C. reduction was 973 μmol $O_2$/g catalyst; O/Co=0.503, mol/mol.

These data are summarized in Table 3.

TABLE 3

| EXAMPLES | $HNO_3$ mol %[1] | R.T.[2] SOAK TIMES, hr | DRYING TEMPS, ° C. | DRYING TIMES, hr | % REACTION[3] | O/Co mol/mol[4] |
|---|---|---|---|---|---|---|
| 3(a) | 0 | 6 | 100 | O/N[5] | 87.0 | 0.728 |
| 3(b) | 20 | 6 | 100 | O/N | 93.2 | 0.579 |
| 3(c) | 0 | O/N | 100 | 7 | 86.9 | 0.727 |
| 3(d) | 20 | O/N | 100 | 7 | 92.6 | 0.503 |

Notes:
[1]Relative to glyoxal.
[2]R.T. = room temperature.
[3]Calculated from elemental analyses for Co and N, assuming that N is present as the cobalt precursor, $Co(NO_3)_2$.
[4]A standard test of $O_2$ chemisorption (with temperature quenching at −77° C. to minimize oxidation) preceded by a standard 450° C. reduction routine.
[5]O/N = overnight, generally about 17–18 hr.

EXAMPLE 4

The following describes a series of catalyst preparations. The first five of these preps, i.e., 4(a) through 4(e), calls for a first step two-day treatment at ambient temperature, beyond which period one of the catalyst preps, i.e., 4(a), is followed up immediately by a drying step, others by extension of the two day treatment by an additional one or two days of treatment, respectively, at ambient temperature, i.e., 4(b)/4(c), and another at elevated temperature, i.e., 4(d), and then by the drying step. In accordance with 4(e) the step 2 portion of the preparation combines with the ambient two day ambient temperature treatment an added nitric acid treatment followed by the drying step. The final prep 4(f) demonstration calls for an initial step which includes a 4 hour treatment at 60° C., an overnight treatment at ambient temperature, and a final 4 hour treatment at 60° C. to completion. There is no step 2 preparation; the step one preparation being followed by an overnight drying step at 110° C. The specific preparations are described hereafter, and the results of these tests are summarized in Table 4.

4(a) R.T./2 days:

A solution was made from 57.78 g $Co(NO_3)_2 \cdot 6H_2O$ (Aldrich, 99%), 2.00 g aqueous $HReO_4$ (Aldrich; 65–70 wt %), and 30.25 g aqueous glyoxal (Aldrich; 40 wt %; 1.05:1 mol:mol ratio to $Co(NO_3)_2 \cdot 6H_2O$).

90.00 g of the solution was mixed with 12.00 g fumed $SiO_2$ (EH-5 grade; Cabot Corporation), and the resulting wet mixture was separated into 5 approximately equal portions. After each portion spent 2 days at room temperature, after which evolution of $NO_x$ by-product had ceased, one portion was dried for approximately a day at 100° C. The friable solid was reduced to a powder by milling one minute in a small laboratory analytical mill (Janke & Kunkel).

The milled solid had a loose bulk density of 0.8083 g/cc, surface area of 166 m²/g, pore volume of 0.256 ml/g, and analyzed for 9.37 wt % C, 23.41 wt % Co and 0.81 wt % N (92.7% reaction). Temperature quenched $O_2$ chemisorption after standard 450° C. reduction was 1178 μmol $O_2$/g catalyst; 0/Co=0.593, mol/mol.

4(b) R.T./2 days +additional 1 day at R.T:

After spending 2 days at room temperature as described in (a), an aliquot of wet mixture was allowed to spend an additional day at room temperature before drying and milling as in (a).

The milled solid had a loose bulk density of 0.7161 g/cc, surface area of 136 m²/g, pore volume of 0.334 ml/g, and analyzed for 9.60 wt % C, 23.65 wt % Co and 0.54 wt % N (95.2% reaction). Temperature quenched $O_2$ chemisorption after standard 450° C. reduction was 909 μmol $O_2$/g catalyst; O/Co=0.453, mol/mol.

4(c) R.T./2 days+additional 2 days at R.T:

After spending 2 days at room temperature as described in (a), an aliquot of wet mixture was allowed to spend an additional 2 days at room temperature before drying and milling as in (a).

The milled solid had a loose bulk density of 0.6327 g/cc, surface area of 99 m²/g, pore volume of 0.329 ml/g, and analyzed for 10.36 wt % C, 26.00 wt % Co and 0.69 wt % N (94.4% reaction). Temperature quenched $O_2$ chemisorption after standard 450° C. reduction was 862 μmol $O_2$/g catalyst; O/Co=0.391, mol/mol.

4(d) R.T./2 days+additional 1 day at 90° C.:

After spending 2 days at room temperature as described in (a), an aliquot of wet mixture was allowed to spend an additional day at 90° C. before drying and milling as in (a).

The milled solid had a loose bulk density of 0.5754 g/cc, surface area of 103 m²/g, pore volume of 0.407 ml/g, and analyzed for 9.90 wt % C, 22.89 wt % Co and 0.36 wt % N (96.7% reaction). Temperature quenched $O_2$ chemisorption after standard 450° C. reduction was 569 μmol $O_2$/g catalyst; O/Co=0.293, mol/mol.

4(e) R.T./2 days+additional 1 day at R.T+added concentrated $HNO_3$:

After spending 2 days at room temperature as described in (a), an aliquot of wet mixture was allowed to spend an additional day at room temperature after mixing in 5.03 g concentrated $HNO_3$ (ca. 70 wt %). It was then dried and milled as in 4(a).

The milled solid had a loose bulk density of 0.3200 g/cc, surface area of 107 m²/g, pore volume of 0.472 ml/g, and analyzed for 9.57 wt % C, 24.33 wt % Co and 0.23 wt % N (98.0% reaction). Temperature quenched $O_2$ chemisorption after standard 450° C. reduction was 385 μmol $O_2$/g catalyst; O/Co=0.187, mol/mol.

4(f) 60° C. Slurry Preparation:

A solution was made from 34.04 g $Co(NO_3)_2 \cdot 6H_2O$ (Aldrich, 99%), 17.83 g aqueous glyoxal (Aldrich; 40 wt %; 1.05:1 mol:mol ratio to $Co(NO_3)_2 \cdot 6H_2O$), and 3 drops of concentrated $HNO_3$ (Mallinckrodt, 70.2 wt %).

49.39 g of the solution was mixed with 2.00 g fumed $SiO_2$ (EH-5 grade; Cabot Corporation), along with another 6 drops of concentrated $HNO_3$ to initiate action. After 4 hr with stirring of the slurry at 60° C., evolution of reddish-brown $NO_2$ gave evidence that reaction had started. The slurry was cooled to room temperature, and the reaction was allowed to proceed overnight. The next morning, about 1 ml of deionized water was added to the now relatively thick mixture to allow stirring, and the stirred mixture was heated at 60° C. until $NO_2$ no longer evolved from the mixture. The mixture was then dried overnight in a vacuum oven set at 100° C. The friable solid was reduced to a powder by milling one minute in a small laboratory analytical mill (Janke & Kunkel).

The milled solid had a loose bulk density of 0.3345 g/cc, surface area of 24 m²/g, pore volume of 0.3879 ml/g, and analyzed for 12.91 wt % C, 29.48 wt % Co and 0.022 wt % N (99.8% reaction). Temperature quenched $O_2$ chemisorption after standard 450° C. reduction was 0.0 μmol $O_2$/g catalyst.

prep mixture should not be allowed to sit at the highly acidic conditions created by the $HNO_3$ by-product; shown by comparison of 4(b) and 4(c) with 4(a). It is also evident that at somewhat elevated temperature the loss in activity is more acute, 4(d). Adding additional $HNO_3$ to the $HNO_3$ that is produced as a by-product is to be avoided.

Preparations should avoid practices that cause dissolution and recrystallization of the cobalt oxalate product during catalyst preparation because this is the mechanism of dispersion loss. Hence, during the preparations, it is desirable to combine relatively short reaction times with relatively low liquid volumes and relatively low temperatures, while at the same time removing the by-product $HNO_3$ as quickly as possible, which will promote higher metal dispersions. The combinations of variables which will preserve metal dispersions after completion of the reaction will also be beneficial in promoting metal dispersions during the reaction.

Preparation procedures that are conducted at moderately elevated temperatures, e.g., 100° C., are generally preferred. This is because the rate of reaction is increased, despite the increased temperature and increased concentration of by-product $HNO_3$. Drying and reaction thus occur simultaneously thereby minimizing the instantaneous liquid volume and $HNO_3$ by-product concentration.

The following describes the preparation of a series of four catalysts two of which were treated with a glyoxal promoter, and two which were not so treated. The four catalysts were then treated in similar fixed bed hydrocarbon synthesis runs, at similar conditions for comparative purposes.

EXAMPLE 5

Four catalysts for use in hydrocarbon synthesis Runs 011, 012, 014 and 018, respectively, were prepared. The method of preparation and the characteristics of the catalysts used in the four runs are given as follows:

Catalyst of Runs 011 and 012:

A solution was made from 85.52 g $Co(NO_3)_2 \cdot 6H_2O$ (Aldrich, 99%), 2.97 g aqueous $HReO_4$ (Aldrich; 65–70 wt %), and 29.99 g aqueous glyoxal (Aldrich; 40 wt %; 0.70:1 mol:mol ratio to $Co(NO_3)_2 \cdot 6H_2O$).

66.51 g of the solution was mixed at 40° C. with 10 g fumed $SiO_2$ (EH-5 grade; Cabot Corporation), and the

TABLE 4

| EXAMPLES | STEP 1 OF PREPARATION | STEP 2 OF PREPARATION | FOLLOW-UP DRYING[1] | % REACTION[2] | O/Co (mol/mol)[3] |
|---|---|---|---|---|---|
| 4(a) | ~2 Days @ R.T.[4] | NONE | 100° C./~1 day | 92.7 | 0.593 |
| 4(b) | ~2 Days @ R.T.[4] | 1 day @ R.T. | 100° C./~1 day | 95.2 | 0.453 |
| 4(c) | ~2 Days @ R.T.[4] | 2 day @ R.T. | 100° C./~1 day | 94.4 | 0.391 |
| 4(d) | ~2 Days @ R.T.[4] | 1 day @ 90° C. | 100° C./~1 day | 96.7 | 0.293 |
| 4(e) | ~2 Days @ R.T.[4] | 1 day @ R.T.; $HNO_3$ | 100° C./~1 day | 98.0 | 0.187 |
| 4(f) | 60° C./4 hr + R.T./overnight + 60° C. to completion | NONE | 110° C./overnight | 99.8 | 0.0 |

Notes:
[1]Drying followed the reaction.
[2]Calculated from elemental analyses for Co and N, assuming that N is present as the cobalt precursor, $Co(NO_3)_2$.
[3]A standard test of $O_2$ chemisorption (with temperature quenching at −77° C. to minimize oxidation) preceded by a standard 450° C. reduction routine.
[4]R.T. = room temperature.

From these data is can be concluded that some preparation techniques can be helpful (and others avoided) in obtaining high metals dispersions, as indicated by the O/Co ratios obtained. For example, on completion of the reaction, the resulting mixture was first allowed to sit for 6 hr at room temperature, then placed into a vacuum oven set at 110° C. overnight. The friable solid was reduced to a powder by milling one minute in a small laboratory analytical mill (Janke & Kunkel).

The milled solid was calcined at 300° C. for 1 hr. The calcined catalyst had a loose bulk density of 0.7414 g/cc, surface area of 209 m$^2$/g, pore volume of 0.7718 ml/g, and analyzed for 38.38 wt % Co and 3.27 wt % Re. Temperature quenched O$_2$ chemisoxption after standard 500° C. reduction was 1902 μmol O$_2$/g catalyst; O/Co=0.584, mol/mol.

Catalyst of Run 014:

A solution was made from 513 g Co(NO$_3$)$_2$·6H$_2$O (Aldrich, 99%), 17.83 g aqueous HReO$_4$ (Aldrich; 65–70 wt %), and 108.01 g deionized water.

119.56 g of the solution was mixed in increments with 20 g filmed SiO$_2$ (EH-5 grade; Cabot Corporation), and the resulting mixture was dried in a vacuum oven set at 110° C. overnight. The friable solid was reduced to a powder by milling one minute in a small laboratory analytical mill (Janke & Kunkel).

The milled solid was calcined at 300° C. for 3 hr. The calcined catalyst had a loose bulk density of 0.7497 g/cc, surface area of 174 m$^2$/g, pore volume of 0.6351 ml/g, and analyzed for 40.49 wt % Co and 3.04 wt % Re. Temperature quenched O$_2$ chemisorption after standard 375° C. reduction was 1163 μmol O$_2$/g catalyst (843 after 450° C. reduction); O/Co=0.339, mol/mol.

Catalyst of Run 018:

A solution was made from 513 g Co(NO$_3$)$_2$·6H$_2$O (Aldrich, 99%), 17.83 g aqueous HReO$_4$ (Aldrich; 65–70 wt %), and 108.01 g deionized water.

Silica gel (60×200 mesh Davison Grade 62; 273 m$^2$/g, 1.2359 ml/g) was vacuum dried at 100° C. for 2 days, then impregnated to incipient wetness with the solution in three steps with overnight drying in between in a vacuum oven set at 110° C. In all, 221.42 g of solution were added to 40.51 g of silica gel.

The dried solid was calcined at 300° C. for 3 hr, then reduced to a powder by milling in one minute segments in a small laboratory analytical mill (Janke & Kunkel), and collecting −45μ powder with a Sonic Sieve instrument, then passing the +45μ solids back through the analytical mill.

The powdered catalyst had a loose bulk density of 0.4789 g/cc, surface area of 146 m$^2$/g, pore volume of 0.4991 ml/g, and analyzed for 35.28 wt % Co and 3.32 wt % Re. Temperature quenched O$_2$ chemisorption before milling and after standard 375° C. reduction was 1189 μmol O$_2$/g catalyst (1087 after 450° C. reduction); O/Co=0.363, mol/mol.

These catalysts were employed in Runs 011, 012, 014 and 018 conducted at 221.1° C., 280 psig, with a synthesis gas feed of 65% H$_2$–31% CO-4% Argon tracer, and space velocity adjusted to give a % CO conversion of at least 85% at the beginning of the run. In conducting these tests, the catalysts were diluted with a minimum of 150:1 parts by weight of quartz sand to minimize temperature gradients in the reaction zone of a fixed bed reactor; the reaction zone constituting an annular zone between concentric tubes, the radius of the inner tube of which approximates 0.25 inch, and the radius of the outer tube of which approximates 0.70 inch. The % CO conversion and selectivity to methane (mole % of CO converted to CH$_4$) is shown in the table. Values for "cobalt productivity", which has the units of liters of CO converted per hour per gram of catalytic metal, is included in Table 5A/5B.

TABLE 5A

| Run No. | Wt % Co | Wt % Re | Promoter/Ratio[a] |
|---|---|---|---|
| 011 | 38.38 | 3.27 | Glyoxal/0.703 |
| 012 | 38.38 | 3.27 | Glyoxal/0.703 |
| 014 | 40.49 | 3.04 | NONE |
| 018 | 35.28 | 3.32 | NONE[b] |

[a]Mol:mol glyoxal:Co(NO$_3$)$_2$.
[b]This catalyst was ground to an average particle size of about 12 microns to be more similar in size to the catalyst used in Runs 011, 012 and 014.

TABLE 5B

| Run No. | Run Temp, ° C. | Days to Line Out (c) | Data Period/Days | % Co Conv. | Reduced Catalyst Prod. (d) | Co Prod. (e) | CH$_4$ Sel. (f) | Data Type (g) |
|---|---|---|---|---|---|---|---|---|
| 011 | 221.1 | 5.0 | 2.30 | 94.1 | 5026 | 11.14 | 5.26 | NSSD |
|  |  |  | 3.06 | 93.0 | 4969 | 11.02 | 5.27 | NSSD |
|  |  |  | 6.07 | 90.1 | 4814 | 10.68 | 5.34 | SS |
|  |  |  | 9.76/0.5 | 87.4 | 4666 | 10.34 | 5.34 | SS |
| 012 | 221.1 | 7.0 | 1.79 | 94.0 | 4869 | 10.80 | 5.38 | NSSD |
|  |  |  | 2.93 | 93.0 | 4817 | 10.68 | 5.43 | NSSD |
|  |  |  | 6.47 | 90.0 | 4658 | 10.33 | 5.59 | NSSD |
|  |  |  | 13.52/0.5 | 88.8 | 4596 | 10.19 | 5.26 | SS |
| 014 | 221.1 | ~5 days (h) | 1.61 | 85.8 | 4288 | 8.94 | 4.83 | NSSD |
|  |  |  | 1.90 | 85.0 | 4251 | 8.86 | 4.81 | NSSD |
|  |  |  | 3.25 | 80.1 | 4003 | 8.35 | 4.85 | NSSD |
|  |  |  | 7.73 | 75.0 | 3750 | 7.82 | 4.76 | SS |
|  |  |  | 8.02/0.5 | 74.8 | 3738 | 7.79 | 4.76 | SS |
|  |  |  | 9.18 | 70.7 | 3536 | 7.37 | 4.94 | SS |
| 018 | 221.1 | ~5 days (h) | 0.64 | 90.0 | 3584 | 8.76 | 6.23 | NSSD |
|  |  |  | 1.06 | 87.0 | 3464 | 8.47 | 6.50 | NSSD |
|  |  |  | 1.28 | 85.0 | 3386 | 8.28 | 6.56 | NSSD |
|  |  |  | 2.17 | 80.0 | 3185 | 7.78 | 6.62 | NSSD |
|  |  |  | 4.20 | 75.0 | 2985 | 7.30 | 6.63 | NSSD |
|  |  |  | 8.01/0.5 | 70.3 | 2799 | 6.84 | 6.64 | SS |

The following can be concluded from these data:

At ~86–89% conversion, the duplicate data for the glyoxal promoted catalyst show Co Productivities of 10.34 and 10.19, as compared to 8.94 and 8.47 for the unpromoted and conventional silica catalysts, respectively. Reduced Catalyst Productivity leads to the same conclusion, even when it is taken into account that the conventional silica catalyst contains a little less Co. $CH_4$ Selectivities fall in the order of unpromoted catalyst (4.83) <promoted catalysts (5.34, 5.26) <<unpromoted conventional silica (6.50).

However, an important point: The glyoxal promoted catalyst was well into steady state, with data being taken 10–14 days into the Runs, whereas the unpromoted catalyst data was taken less than 2 days into the runs. This was done so that comparisons could be made at similar conversion levels. However, this then biases the unpromoted catalyst data toward an overestimate of activity, since they are not lined out after 2 days. At steady state, the unpromoted catalyst Co Productivities are substantially less: 7.37 and 6.84, respectively, at run times in excess of 8 days more nearly similar to glyoxal promoted catalyst data. (Even then, there is still the bias of much lower conversion for the unpromoted catalysts.)

Having described the invention, what is claimed is:

1. A process for the preparation of a catalyst useful for conducting carbon monoxide conversion reactions which comprises dispersing in a liquid a preformed, particulate refractory inorganic oxide support, a compound or salt of a catalytic metal, or metals, an oxidizable alcohol, oxidizable aldehyde, or oxidizable ketone promoter, and an oxidant sufficient to oxidize said promoter to form polyfunctional carboxylic acids which react in situ with the metal, or metals, compound or compounds at acidic conditions to precipitate on the surface of the support an insoluble highly dispersed carboxylate salt, or salts, of said catalytic metal, or metals, separating and recovering the solids from the liquid, and heating the solids to form a catalyst composite which, in reduced form, is more active, and more selective, in conducting similar carbon monoxide hydrogenation reactions at the same reaction conditions than catalysts of similar composition, similarly prepared except that the compound or salt of the catalytic metal, or metals, has not been contacted and treated with said oxidizable alcohol, oxidizable aldehyde, or oxidizable ketone promoter.

2. The process of claim 1 wherein the catalytic metal, or metals, of the solids are heated and reduced to the zero-valent state.

3. The process of claim 2 wherein the solids are heated in a vacuum or in an inert atmosphere.

4. The process of claim 2 wherein the solids are heated in an oxidizing atmosphere in a first step to form an oxide of the catalytic metal, or metals, and the solids are heated in a reducing atmosphere in a second step to bring the catalytic metal, or metals, to the zero-valent state.

5. The process of claim 1 wherein the catalytic metal, or metals, component of the catalyst is selected from Groups IB, IIB, VIIB, and VIII of the Periodic Table of the Elements, and the catalyst contains from about 10 percent to about 80 percent, by weight, and higher, of the catalytic metal, or metals.

6. The process of claim 1 wherein the refractory inorganic oxide support component of the catalyst is silica, and the catalytic metal, or metals, component of the catalyst is a Group VIII metal.

7. The process of claim 6 wherein the support component of the catalyst is fumed silica, and the Group VIII metal is cobalt.

8. The process of claim 1 wherein the oxidizable promoter is glyoxal.

9. The process of claim 8 wherein the molar ratio of glyoxal:catalytic metal, or metals, ranges from about 0.1:1 to about 5.0:1.

10. The process of claim 1 wherein the oxidant is selected from the group consisting of $HNO_3$, $H_2O_2$ and nitrate salts of a catalytic metal, or metals, and the refractory inorganic oxide support is selected from the group consisting of alumina, silica, silica-alumina, fumed silica, titania, and zirconia, and their mixed oxides.

11. A catalyst useful for conducting carbon monoxide hydrogenation reactions made by the steps comprising dispersing in a liquid a preformed, particulate refractory inorganic oxide support, a compound or salt of a catalytic metal, or metals, an oxidizable alcohol, oxidizable aldehyde, or oxidizable ketone promoter, and an oxidant sufficient to oxidize said promoter to form polyfunctional carboxylic acids which react in situ with the metal, or metals, compound or compounds at acidic conditions to precipitate on the surface of the support an insoluble highly dispersed carboxylate salt, or salts, of said catalytic metal, or metals, separating and recovering the solids from the liquid, and heating the solids to form a catalyst composite which, in reduced form, is more active, and more selective, in conducting similar carbon monoxide hydrogenation reactions at the same reaction conditions than catalysts of similar composition, similarly prepared except that the compound or salt of the catalytic metal, or metals, has not been contacted and treated with said oxidizable alcohol, oxidizable aldehyde, or oxidizable ketone promoter.

12. The catalyst of claim 11 wherein the catalytic metal, or metals, of the solids are heated and reduced to the zero-valent state.

13. The catalyst of claim 11 wherein the catalytic metal, or metals, component of the catalyst is selected from Groups IB, IIB, VIIB, and VIII of the Periodic Table of the Elements, and the catalyst contains from about 10 percent to about 80 percent, and higher, of the catalytic metal, or metals.

14. The catalyst of claim 11 wherein the refractory inorganic oxide support component of the catalyst is silica, and the catalytic metal, or metals, component of the catalyst is a Group VIII metal.

15. The catalyst of claim 11 wherein the support component of the catalyst is fumed silica, the Group VIII metal is cobalt, and the oxidizable promoter is glyoxal.

* * * * *